(12) United States Patent
Schmidt

(10) Patent No.: US 7,981,632 B2
(45) Date of Patent: Jul. 19, 2011

(54) SEQUENTIALLY ARRANGED STREPTAVIDIN-BINDING MODULES AS AFFINITY TAGS

(75) Inventor: Thomas Schmidt, Adelebsen (DE)

(73) Assignee: IBA GmbH (DE)

( * ) Notice: Subject to any disclaimer, the term of this patent is extended or adjusted under 35 U.S.C. 154(b) by 934 days.

(21) Appl. No.: 10/026,578

(22) Filed: Dec. 17, 2001

(65) Prior Publication Data

US 2003/0083474 A1    May 1, 2003

(30) Foreign Application Priority Data

Mar. 21, 2001  (DE) .................................. 101 13 776
Oct. 12, 2001  (WO) ....................... PCT/EP01/11846

(51) Int. Cl.
  *G01N 33/53* (2006.01)
(52) U.S. Cl. ......... 435/7.5; 435/7.1; 435/69.1; 530/350; 530/388.25
(58) Field of Classification Search ............... 424/192.1; 435/69.1, 7.1, 6, 320.1, 325, 252.3; 530/350, 530/300
See application file for complete search history.

(56) References Cited

U.S. PATENT DOCUMENTS

| | | | |
|---|---|---|---|
| 5,292,646 A | | 3/1994 | McCoy et al. |
| 5,310,663 A | | 5/1994 | Dobeli et al. |
| 5,506,121 A | * | 4/1996 | Skerra et al. .................. 435/69.7 |
| 5,654,176 A | | 8/1997 | Smith |
| 6,103,493 A | * | 8/2000 | Skerra et al. .................. 435/69.1 |
| 6,841,359 B2 | * | 1/2005 | Szostak et al. ............... 435/69.1 |

FOREIGN PATENT DOCUMENTS

| | | |
|---|---|---|
| DE | 20011013776 | 3/2001 |
| EP | 0 965 597 A1 | 12/1999 |
| WO | WO 97/25345 | 7/1997 |
| WO | WO 01/98366 | 12/2001 |
| WO | WO 02/38580 | 5/2002 |

OTHER PUBLICATIONS

Wells, Biochemistry, vol. 29, pp. 8509-8517, 1990.*
Srisawat et al. (RNA, 2001, vol. 7, pp. 632-641).*
Anthony D. Keefe and Jack W. Szostak; The Use of mRNA Display to Select High-Affinity Protein-Binding Peptides; PNAS, Mar. 27, 2001, vol. 98(7); 3750-3755.
Anthony D. Keefe, et al.; One-Step Purification of Recombinant Proteins Using a Nanomolar-Affinity Streptavidin-Binding Peptide, the SBP-Tag; PNAS 2001, 23:440-446.
2000, vol. 28, No. 21, Aug. 29, 2000, Complete genome sequence of the alkaliphillic bacterium *Bacillus halodruans* and genomic sequence comparison with *Bacillus subtilis*.
Arne Skerra, et al.; Applications fo a peptide ligand for strptavidin: the Strep-tag; 1999; 79-86.
David Wilson, et al.; The use of mRNA display to select high-affinity protein-binding peptides; Mar. 27, 2001; 3750-3755.
Thomas Schmidt et al.; Molecular interaction between the Strep-tag affinity peptide and its cognate target, streptavidin; 1996; 753-766.
Bradley Katz, et al.; Topochemisty for preparing ligands that dimerize receptors; Sep. 1995; 93-100.
Bradley Katz; Streptavidin-binding and -dimerizing ligands discovered by phage display, topchemisty, and structure-base design; 1999; 57-65.
Julie Brown, et al.; Construction and Characterization of a Quadruplex DNA Selective Single-Chain Autoantibody from a Viable Motheaten Mouse Hybridoma with Homology to Telomeric DNA Binding Proteins; 1998; 16338-16348.
Brian Kay, et al.; An M13 phage library displaying random 38-amino-acid peptides as a source of novel sequences with affinity to selected targets; 1993; 59-65.
Schmidt & Skerra, Use of the Strep-Tag and Streptavidin for Detecation and Purificarion of Recombinant Proteins, Methods in Enzymology 326:271-304 (2000).
Junttila et al., Proteomics 5:1199-1203 (2005).
One-Strep Kit Manual (version PR13-0007 IBA GmbH (2006).
Ford, et al., "Fusion Tails for the Recovery and Purification of Recombinant Proteins," Protein Expression and Purification, 2:95-107 (1991).
Hernan et al., "Multiple Epitope Tagging of Expressed Proteins for Enhanced Detection," BioTechniques, 28:789-793 (2000).
Jarvik et al., "Epitope Tagging," Annu. Rev. Genet. 32:601-618 (1998).
Creighton, Proteins, Structure and Molecular Properties, 2nd Edition, 1993, W.H. Freemann and Company, New York p. 338.

* cited by examiner

*Primary Examiner* — Hope A Robinson
(74) *Attorney, Agent, or Firm* — Michael A. Whittaker; Acuity Law Group, P.C.

(57) ABSTRACT

The present invention relates to sequentially arranged streptavidin-binding binding modules which may in particular be used as affinity tags. The affinity tags comprise at least two individual modules capable of mediating avidic binding to streptavidin.

17 Claims, 6 Drawing Sheets

SEQUENTIALLY ARRANGED STREPTAVIDIN-BINDING MODULES AS AFFINITY TAGS

CROSS-REFERENCE TO RELATED APPLICATIONS

This application claims priority to PCT Application No. PCT/EP01/11846, filed Oct. 12, 2001, and to German Application No. 10113776.1, filed Mar. 21, 2001.

The present invention relates to sequentially arranged streptavidin binding peptide modules which may in particular be used as affinity tags. The affinity tags comprise at least two individual modules capable of mediating avidic binding to streptavidin.

Many projects on resolving genomes of various organisms are close to completion. Thus the human genome has almost completely been sequenced recently and the sequence data has been classified and worked up (published in i) Nature, Vol. 409, Feb. 15, 2001, ii) Science, Vol. 291, No. 5507, Feb. 16, 2001). One of the next challenges will be the elucidation of the in each case corresponding proteomes, i.e. the elucidation of the protein functions corresponding to the genome and their dynamic interaction for the generation of cellular functions.

With the aid of modern genetic methods it is possible to clone almost any natural gene and to produce the corresponding protein recombinantly in microorganisms or tissue cultures. This allows on the one hand access to proteins which occur in their natural producers only in negligible amounts and which are therefore obtainable from this source only with difficulty, if at all. On the other hand, the recombinant approach also provides a wide variety of possibilities for altering the target protein genetically in order to make it possible thereby to characterize said protein in detail and/or to manipulate it more readily.

A first step in characterizing the target protein is normally its purification from the host proteins, which traditionally can be achieved only by empirical development of a method specific for each protein. In order to establish a detection method which may be important, for example, for optimizing production processes or else may be helpful for further characterization of the target protein downstream, it has been necessary in the past to prepare a specific antiserum against the desired protein; for this purpose, however, the target protein in turn had to be prepared initially as pure substance. Further methods for downstream analysis of recombinant proteins often require immobilization as irreversible as possible to a solid phase such as, for example, in the wells of a microtiter plate or in the form of "arrays" on chips (protein chips). Since each protein is a substance with individual properties and therefore each protein is affected in a different way during direct immobilization, it is advantageous for the presentation of proteins in native authentic form if immobilization can be achieved by an independent module in a standardized manner.

A universal solution for these questions is in principle based on the slight modification of a recombinant gene during cloning with nucleotide sequences which code for "peptide tags". It is important in this connection that the peptide tag has suitable binding properties for a receptor. In practice, utilization of such a peptide tag is as follows:

After or during expression, the target protein of interest is modified by a peptide tag. The known and well-characterized properties of the peptide tag for binding to its receptor in various assay methods are then available for further analysis of the target protein. Normally, the affinity tag is initially used for purifying the fusion protein by means of an immobilized receptor. It is important for purification by affinity chromatography that the recombinant fusion protein can again be eluted from the solid phase under mild conditions. After purification it may be desirable to be able to utilize the peptide tag for immobilizing the recombinant target protein to a solid phase such as the wall of a microtiter plate well, for example. Normally, a particularly tight binding is desired here, i.e. the fusion protein should not detach again from the solid phase under any circumstances during the assay method.

A commonly used peptide tag is the $His_6$ tag. This tag binds to heavy metal ions such as nickel, for example, with chelate formation. A problem occurring when using this tag in the purification of proteins is contamination of the desired protein with the heavy metals used as receptors. Furthermore, chelate formation between heavy metal receptor and $His_6$ tag represents only low specificity binding. Removing the tag requires high concentrations of imidazole which in many applications may also constitute a problem. All in all, using $His_6$ tags has so far produced purity degrees of about 80% of the desired protein.

U.S. Pat. No. 5,506,121, for example, has disclosed another class of peptide tags having a specific binding property for streptavidin as receptor. These peptide tags have been denoted STREP-TAG® and are sold worldwide under this name.

The development of these affinity tags was based on the observation of Devlin et al. (1990) and Lam et al. (1991) that streptavidin is capable of binding peptides at all. The authors regarded the 3 amino acid peptide sequence $NH_2$-His-Pro-Gln(Met, Asn)-COOH as the smallest motif for streptavidin binding. However, it was impossible to use such peptides alone for practical applications, since the binding affinity was too low (Weber at al., 1992). Only after Schmidt and Skerra (1993) optimized the affinity practical applications did become possible (see also U.S. Pat. No. 5,506,121).

Despite the optimization by Schmidt and Skerra (1993) there were still problems in particular application formats and/or due to different effects of various fusion proteins on streptavidin binding affinity (Schmidt and Skerra, 1994). In particular, it turned out that the initially most preferred streptavidin-binding peptide having the sequence $NH_2$-Trp-Arg-His-Pro-Gln-Phe-Gly-Gly-COOH (SEQ ID NO:1) (STREP-TAG®) could be used only on the free C-terminal end of the recombinant protein fusion partner, since the C-terminal carboxylate group formed an ionic interaction with an arginine residue of streptavidin (Schmidt et al., 1996). For the more general application, the peptide sequence $NH_2$-Trp-Ser-His-Pro-Gln-Phe-Glu-Lys-COOH (SEQ ID NO:2) (STREP-TAG® II) proved more suitable, since it was possible to utilize this sequence independently of the location on the recombinant fusion protein partner. However, the affinity of the STREP-TAG® II/streptavidin complex was lower than the affinity of the STREP-TAG® II/streptavidin complex (Schmidt et al., 1996).

Therefore, the receptor streptavidin was optimized with respect to better STREP-TAG® II binding. It was possible to generate streptavidin muteins which have distinctly higher STREP-TAG® II affinity and which have been disclosed in U.S. Pat. No. 6,103,493 and by Voβ and Skerra (1997). These streptavidin muteins are commercially available under the name STREP-TACTIN®. The affinity tag technology based on STREP-TAG® II/STREP-TACTIN® interaction ($K_d$=approx. $1·10^{-6}$ M, Voβ and Skerra, 1997) is markedly improved for many practical applications compared with the affinity tag technology based on STREP-TAG®/streptavidin interaction ($K_d$=approx. $3.7·10$ M, Schmidt et al., 1996). Nevertheless, there are still limitations if a particularly tight immobilization is desired. This is the case, for example, for the immobilization of recombinant STREP-TAG® II fusion proteins on STREP-TACTIN®-coated microtiter plates or on so-called "protein chips" on which the recombinant proteins, being immobilized in this standardized manner, are then intended to be analyzed in the most complex assay methods or when the recombinant fusion protein which in the extreme problem case is present only in very diluted form and is highly contaminated with other host proteins is intended to be purified efficiently, in particular in batch format.

It is impossible for one and the same interaction to meet or optimally meet the different demands made on such a peptide tag receptor interaction, i.e. binding as reversible as possible for gentle purification and also binding as irreversible as possible for the immobilization in diagnostic assay systems in microtiter plate format or on protein chips.

Trying, therefore, to solve the problem by generating a generally optimally functioning peptide tag/receptor interaction on monovalent basis presents a dilemma: if binding becomes strong enough for tight binding to surfaces, then it may be impossible to carry out efficient elution under competitive conditions during affinity chromatographic purification. Competitive elution, however, is an elementary condition for being able to carry out affinity chromatographic elution specifically, efficiently and gently (see, for example, Skerra and Schmidt, 1999). The dilemma is caused by each interaction being determined by a binding rate and a dissociation rate. A general principle is that immobilization on surfaces prefers very slow dissociation rates, whereas affinity chromatographic elution by a competitively (competitively means that both ligands can bind separately but not simultaneously) binding agent prefers comparatively rapid dissociation rates. That is to say therefore, an ideal affinity tag should behave under competitive conditions as if it had a fast receptor dissociation rate and should have a very slow dissociation rate under non-competitive conditions.

It was therefore an object of the invention to develop short peptide sequences which can be linked to a recombinant protein without interfering with the function thereof, which make detection using a readily available reagent possible, which display readily controllable binding properties and which can readily be eluted under competitive conditions despite strong binding affinity to surfaces.

According to the invention, this object is achieved by an isolated streptavidin-binding peptide, wherein the peptide comprises the sequential arrangement of at least two streptavidin-binding or/and streptavidin mutein-binding modules. The at least two modules can either be different or identical. In one preferred embodiment each of these at least two binding modules has a binding affinity of at least $K_d \leq 10$ mM. It is furthermore preferred that at least one binding module binds competitively with biotin. In another preferred embodiment, each of the binding modules binds competitively with biotin. In a preferred embodiment such a peptide is capable of cooperatively binding to a single streptavidin tetramer or streptavidin dimer.

In a preferred embodiment, at least one individual streptavidin-binding module of the peptide of the invention comprises the sequence -His-Pro-.

In a further preferred embodiment, at least one of the individual streptavidin-binding modules comprises the sequence -His-Pro-Gln-. In this respect, it is noted that a scientific article of Wilson et al. (2001), which was published after the priority date of the present application, describes streptavidin binding peptides which comprise one or two -His-Pro-Gln- motifs.

Preferably the distance between the two individual modules of the peptides disclosed here is at least 0 and not greater than 50 amino acids.

A further preferred embodiment is directed to a peptide comprising at least two streptavidin-binding individual modules or epitopes, wherein the distance between the two individual modules is at least 0 and not greater than 50 amino acids and wherein each individual module includes at least the sequence -His-Pro-Baa- where Baa is glutamine or asparagine or methionine.

An achievement of the invention is therefore the use of streptavidin-binding ditags or multitags. This means the sequential arrangement of at least two different or identical streptavidin-binding or/and streptavidin mutein-binding modules (epitopes) which can be employed as fusion partners of the recombinant target protein. Surprisingly, it is possible by such an arrangement to achieve an avidity effect by divalent or multivalent binding of a ditag or multitag to a homotetrameric STREP-TACTIN® or streptavidin molecule or another streptavidin mutein molecule. Such avidity effects have been known so far primarily for immunoglobulins, since these can adapt through their flexible hinge region to the steric requirements of bivalent binding to two epitopes at the same time. In contrast, the structure of tetrameric streptavidin (Weber et al., 1989) is, compared to antibodies, rather stiff and hardly flexible.

The ditags or multitags of the invention are in particular capable of cooperatively binding to in each case a single streptavidin tetramer or streptavidin dimer. The cooperative binding produces an avidity effect, i.e. increased binding of the peptide tags to a streptavidin receptor. It is assumed that when contacting the peptides of the invention, which comprise at least 2 streptavidin-binding individual modules or epitopes, with a streptavidin receptor, initially an interaction between the individual epitopes and the streptavidin receptor binding sites takes place in a conventional manner. Formation of the individual bond in this connection is in each case subject to the law of mass action, the strength of the bond being determined by the particular dissociation constants ($K_d$). However, when breaking a bond between an individual module and a streptavidin receptor, the peptide does not detach from the streptavidin receptor, since the peptide is still bound to the streptavidin receptor by at least one further individual module. Owing to the spatial proximity of the detached individual module to the streptavidin receptor, the detached individual module then rebinds to the streptavidin receptor. Thus, under non-competitive conditions a synergistic or avidic effect can be observed, since rebinding always takes place.

Under competitive conditions, a vacated streptavidin binding site is occupied by another ligand or competitor mostly added in excess so that rebinding cannot take place, owing to displacement effects. This makes it possible to achieve the object of providing 2 different binding affinity strengths at different surrounding conditions (the avid binding strength differing from the monovalent binding strengths more under non-competitive conditions than under competitive conditions).

The peptides of the invention preferably comprise 2, 3 or 4 streptavidin-binding individual modules, particularly preferably 2 or 4 streptavidin-binding individual modules and most preferably 2 streptavidin-binding individual modules.

An essential feature of the peptides of the invention is the fact that they are not 2 separate tags but are a sequential arrangement of at least 2 streptavidin-binding individual modules. In this way, the binding properties are determined by the streptavidin-binding ditag or multitag and are independent of a protein to be fused thereto. In contrast, when using 2 independent tags at the C-terminus and at the N-terminus of a protein or at the same or different termini of dimeric or multimeric protein complexes, the binding properties are dependent on the particular fusion protein(s) (the domains), in particular on the protein folding thereof.

Using the peptide tags of the invention it is possible i) to generate a markedly stronger binding to immobilized streptavidin or streptavidin muteins by sequential arrangement of at least two streptavidin-binding peptides so that the affinity peptide ii) satisfies the common standards for diagnostic immunological assay methods in microtitre plate format, and the same fusion protein with the same ditag can iii) still be competitively eluted efficiently in the affinity chromatographic purification method. In other words: with respect to its binding properties, in particular binding stability, the ditag behaves in the methods described under i) and ii) like a monotag having distinctly higher binding affinity and in the method described under iii) similar to the individual monotags of which the ditag is composed, when considered separately.

Furthermore, the ditag/streptavidin system is particularly interesting, since there is quite a number of streptavidin-binding peptides but also of streptavidin muteins and since it is thereby possible, by making use of all possible combinations, to generate a particularly wide and yet finely subdivided range of binding activities. If, for example, the sequence $NH_2$-Trp-Ser-His-Pro-Gln-Phe-Glu-Lys-Xaa-Xaa-Xaa-Xaa-Xaa-Xaa-Xaa-Xaa-Trp-Ser-His-Pro-Gln-Phe-Glu-Lys-COOH (SEQ ID NO:3) is used, the fusion protein binds particularly strongly to STEP-TACTIN®, in any case more strongly than $NH_2$-Trp-Ser-His-Pro-Gln-Phe-Glu-Lys-Xaa-Xaa-Xaa-Xaa-Xaa-Xaa-Xaa-Xaa-Xaa-His-Pro-Gln-Xaa-Xaa-Xaa-COOH (SEQ ID NO:4) which in turn binds more strongly than $NH_2$-His-Pro-Gln-Xaa-Xaa-Xaa-Xaa-Xaa-Xaa-Xaa-Xaa-Xaa-Xaa-Xaa-His-Pro-Gln-COOH (SEQ ID NO:5). The same peptides again bind more poorly to streptavidin. These combination possibilities make it possible to select for any intended application the combination which produces an affinity for streptavidin or STREP-TACTIN® or to another streptavidin mutein, which is ideally suited to the intended use.

The term "streptavidin" as used herein includes wild-type streptavidin, streptavidin muteins, streptavidin-like polypeptides, unless otherwise stated in the individual case. Under wild-type streptavidin (wt-streptavidin), the amino acid sequence disclosed by Argarana et al., Nucleic Acids Res. 14 (1986) 1871-1882 is referred to. Streptavidin muteins are polypeptides which are distinguished from the sequence of wild-type streptavidin by one or more amino acid substitutions, deletions or additions and which retain the binding properties of wt-streptavidin. Streptavidin-like polypeptides and streptavidin muteins are polypeptides which essentially are immunologically equivalent to wild-type streptavidin and are in particular capable of binding biotin, biotin derivative or biotin analogues with the same or different affinity as wt-streptavidin. Streptavidin-like polypeptides or streptavidin muteins may contain amino acids which are not part of wild-type streptavidin or they may include only a part of wild-type streptavidin. Streptavidin-like polypeptides are also polypeptides which are not identical to wild-type streptavidin, since the host does not have the enzymes which are required in order to transform the host-produced polypeptide into the structure of wild-type streptavidin.

The term streptavidin also includes streptavidin tetramers and streptavidin dimers, in particular streptavidin homotetramers, streptavidin homodimers, streptavidin heterotetramers and strepavidin heterodimers. Each subunit normally has a binding site for biotin or biotin analogues or for streptavidin-binding peptides.

Examples of streptavidins or streptavidin muteins are mentioned, for example, in WO 86/02077, DE 19641876 A1, U.S. Pat. No. 6,022,951, WO 98/40396 and WO 96/24606.

Another application to be preferred for a ditag is the particularly efficient purification of recombinant fusion proteins from diluted solutions in batch format (in contrast to column chromatography format). Due to the significantly increased apparent affinity in comparison with the monotag, the protein in the diluted solution becomes more concentrated on the immobile phase and thus less recombinant fusion protein is lost in the sequential washing steps during which the equilibrium always re-establishes itself. As soon as the competitively binding agent is then added in excess, the ditag-carrying recombinant protein can be eluted efficiently in batch format, too.

"Batch format" means in particular those assay formats in which the eluent does not migrate through a column or bed but in which receptors are attached to a solid phase and during each washing step virtually the entire liquid phase is removed. Examples of a batch format are magnetic beads which carry receptors on their surface and are contacted in a washing step in each case with liquid, and this liquid can then be removed again completely or virtually completely in each washing step. Another example of batch format are protein chips or receptors introduced onto microtitre plates or similar plates.

A minimum binding ditag comprises in one preferred embodiment an isolated peptide which is composed of at least 2 individual modules (epitopes), wherein the distance between both modules is at least 0 and not greater than 50 amino acids and wherein each individual module includes at least the sequence -His-Pro-Baa- where Baa is glutamine, asparagine or methionine.

Using the ditags or multitags of the invention makes it possible to achieve higher affinities for the particular streptavidin or streptavidin mutein than using an individual monotag (for example the better binding one if two different tags were used), even if the better binding module of the two individual modules is used as monotag. In addition, it is also possible to generate finer grading of the affinity range than is possible by monotags. Nevertheless it is possible to elute competitively ditag- or multitag-carrying recombinant fusion proteins efficiently from solid phases coated with a receptor. High flexibility in the grading of the affinity range of the tags of the invention can be achieved in a simple manner and can be obtained in particular by the choice of peptide tag (which can be composed of a number of different or/and identical individual modules), by the choice of receptor/streptavidin and by the choice of the competitor for elution under competitive conditions.

Furthermore it is possible to prepare stable dimeric recombinant proteins in the following arrangement: recombinant protein-ditag-streptavidin (mutein) with a total of four binding sites-ditag-recombinant protein. It is also possible to link two different recombinant proteins stably via such an arrangement.

A preferred application of ditag fusion proteins is a) stable binding of the fusion partner to surfaces coated with streptavidin (mutein) and/or b) efficient purification of ditag fusion proteins from diluted solutions, in particular in batch format (in contrast to column chromatography format). Especially the highly parallel purification on a small scale but with high yields and high degrees of purity and from complex mixtures is a great challenge for affinity tag systems in high throughput formats, which has been met by the ditag approach for streptavidin-binding affinity tags.

In the peptide of the invention the two modules mediating binding to streptavidin are at a distance of at least 0 and not more than 50, preferably at a distance of at least 4, more preferably at least 8 and up to preferably not more than 30, more preferably not more than 20 amino acids. Particular preference is given to the distance between the two individual modules mediating binding to streptavidin being 8 or 12 amino acids. The length of the binding modules is preferably at least 3, more preferably at least 4 and most preferably at least 6 and preferably not more than 15, more preferably not more than 12 and most preferably not more than 8 amino acids.

The amino acids located between the individual modules may be any amino acids. They are preferably naturally occurring amino acids but chemically modified amino acids may also be present. Such chemically modified amino acids may in particular be incorporated in the case of an in vitro expression system.

In the peptide of the invention the streptavidin-binding individual modules are present sequentially, i.e. no protein with a biological function is located between the individual modules but, where appropriate, only a certain number of linker amino acids. Preferred linker amino acids are Gly and Ser, in particular chains which exclusively or mainly, for example >60%, contain Gly and Ser. The linker length can be adjusted to the distance of the binding centers in the particular streptavidin receptor. In a tetrameric streptavidin, for example, two binding sites are located at the front and two binding sites at the back. Preference is therefore given to peptide tags which have 2 or 4 (2+2) binding sites and in between linkers which are just suited to bridging the distance of the binding centers. It is, however, also possible to use a tag comprising an uneven number of individual modules such as 3 or 5. Particular preference is given to peptides having the following structure:

Where appropriate, no or 1 to 50 linker amino acid(s)—binding module with 3 to 15 amino acids, in particular 3 to 8 amino acids—linker region with 0 to 20, in particular 8 to 12 linker amino acids—binding module with 3 to 15, in particular 3 to 8 amino acids—where appropriate, another non-functional peptide region with no or 1 to 50 linker amino acid(s) or, where appropriate, no or 1 to 50 linker amino acids—binding module with 3 to 15 amino acids, in particular 3 to 8 amino acids—linker region with 0 to 20, in particular 8 to 12 linker amino acids—binding module with 3 to 15, in particular 3 to 8 amino acids—linker region with 15 to 40, in particular 18 to 25 linker amino acids—binding module with 3 to 15, preferably 3 to 8 amino acids—linker section with 0 to 20, in particular 8 to 12 linker amino acids—binding module with 3 to 15, in particular 3 to 8 amino acids—where appropriate, linker section with no or 1 to 50 linker amino acid(s).

Besides the two individual modules and the amino acids which are located between the individual modules the peptide of the invention may contain further amino acids which adjoin to one side of at least one of the individual modules. The total length of the isolated peptide of the invention is preferably at least 6 amino acids, more preferably at least 20 amino acids and may be preferably up to 500 amino acids, more preferably up to 100 amino acids and most preferably up to 56 amino acids and in particular up to 40 amino acids.

At least one of the two individual modules which mediate binding to streptavidin is preferably selected from one of the sequences: -His-Pro-, -His-Pro-Gln-, -His-Pro-Gln-Phe- (SEQ ID NO:6), -Oaa-Xaa-His-Pro-Gln-Phe-Yaa-Zaa- (SEQ ID NO:7), where Oaa is Trp, Lys or Arg, Xaa is any amino acid and preferably a naturally occurring amino acid and where either Yaa and Zaa are both Gly or Yaa is Glu and Zaa is Lys or Arg, -Trp-Xaa-His-Pro-Gln-Phe-Yaa-Zaa (SEQ ID NO:8), where Xaa is any amino acid and where either Yaa and Zaa are both Gly or Yaa is Glu and Zaa is Lys or Arg or -Trp-Ser-His-Pro-Gln-Phe-Glu-Lys (SEQ ID NO:9).

The preferred sequentially arranged binding modules provide an increased affinity for streptavidin but can still be removed sufficiently in the competitive assay format.

The peptide of the invention particularly preferably has the sequence Trp-Ser-His-Pro-Gln-Phe-Glu-Lys-(Xaa)$_n$-Trp-Ser-His-Pro-Gln-Phe-Glu-Lys (SEQ ID NO:10), where Xaa is any amino acid and n is an integer from 5 to 20, in particular from 8 to 12, and the sequence Trp-Ser-His-Pro-Gln-Phe-Glu-Lys-(GlyGlyGlySer)$_n$-Trp-Ser-His-Pro-Gln-Phe-Glu-Lys (SEQ ID NO:11), where n is an integer from 1 to 5 and preferably 2 or 3.

Within the scope of the invention it was found that the peptide sequences of the invention have high binding affinity for streptavidin or nuclear streptavidin (a proteolytic cleavage product of streptavidin) (Bayer, E. A., et al., Biochem. J. 259 (1989), 369-376) and for streptavidin muteins, which affinity is in particular higher than the binding affinities of the individual binding modules; at the same time the said peptides can readily be eluted under competitive conditions.

The individual binding modules of the peptide of the invention preferably have a binding affinity $K_d$ for the particular streptavidin receptor of not more than $10^{-2}$, more preferably not more than $10^{-3}$, even more preferably not more than $10^{-5}$ and at least $10^{-13}$, more preferably at least $10^{-10}$, even more preferably at least $10^{-8}$ and most preferably at least $10^{-6}$ M. Elution under competitive conditions is then preferably carried out using a competitor which has a higher affinity for the particular streptavidin receptor, preferably an affinity which is at least one order of magnitude, more preferably at least two orders of magnitude and most preferably at least three orders of magnitude greater. The binding affinity of streptavidin/biotin, for example, is $4 \times 10^{-14}$ M. Owing to the sequential arrangement of the inventive ditags and of the avidity effect connected therewith the use of 2 binding modules which in each case have a binding affinity of $10^{-6}$ M or higher, in particular $10^{-5}$ M or higher, is in particular possible, and despite the low binding affinities of the individual binding modules a strong binding to the streptavidin receptor is obtained under non-competitive conditions.

Particular preference is given to those streptavidin muteins which are described in U.S. Pat. No. 6,103,493 and also in DE 196 41 876.3. These streptavidin muteins have at least one mutation within the region of amino acid positions 44 to 53, based on the amino acid sequence of wild-type streptavidin. Preference is given to muteins of a minimal streptavidin, which start N-terminally in the region of amino acids 10 to 16 of wild-type streptavidin and end C-terminally in the region of amino acids 133 to 142 of wild-type streptavidin. Examples of such streptavidin muteins have a hydrophobic aliphatic amino acid instead of Glu at position 44, any amino acid at position 45, a hydrophobic aliphatic amino acid at position 46 or/and a basic amino acid instead of Val at position 47. Particular preference is given to streptavidin muteins having the sequence Ile-Gly-Ala-Arg (SEQ ID NO:12) or Val-Thr-Ala-Arg (SEQ ID NO:13) at amino acid positions 44 to 47.

The isolated peptide of the invention is preferably used as label (tag) or affinity tag. The invention therefore further relates to a fusion protein comprising an inventive peptide as described above which has at least two individual modules binding to streptavidin or streptavidin muteins linked to a protein. If the peptide sequence of the invention is present in a fusion protein, this fusion protein, too, has a high affinity for streptavidin and can at the same time be readily eluted under competitive conditions.

Besides eluting under competitive conditions, i.e. in the presence of another streptavidin ligand, it is also possible to break the receptor:affinity tag interaction by changing the pH (pH shift), which makes simple elution possible. Under acidic conditions at least one histidine residue of the peptide of the invention is protonated resulting in the breaking up of the receptor:affinity tag interaction.

The peptide sequence of the invention may be located at the carboxy terminal end, at the amino terminal end or within the amino acid sequence of the protein, as long as this is not connected with adverse properties, such as, for example, inhibition or destruction of the biological activity if it is desired to maintain said activity.

The protein present in the fusion protein may be both a complete protein and a protein mutant such as, for example, a deletion mutant or substitution mutant, or else may be only part of a protein. The peptide of the invention may be linked to the desired protein directly or via linker or spacer sequences.

In a further embodiment, the invention refers to a method for detection of a binding event between a protein and an analyte that is capable of binding to the protein by use of a biochip or biosensor. In this method a biochip/biosensor is used on which surface streptavidin or a streptavidin mutein is immobilized. The immobilization of streptavidin or the streptavidin mutein on the surface of the biosensor can occur by any suitable immobilization method and/or coupling chemistry, for example, using the protocol describes by Busch et al. (2000). For one embodiment of this method, the mutein known as STREP-TACTIN® is preferably used.

This method of detection of a binding event between a protein and an analyte takes advantage of the strong binding affinity that the peptide of the invention has to streptavidin or a streptavidin mutein. The method comprises as step (a) contacting a first sample containing a protein which is linked (fused) to a peptide of the present invention (i.e. a peptide that comprise the sequential arrangement of at least two different or identical streptavidin-binding or/and streptavidin mutein-binding modules) with the biosensor, thereby allowing the formation of a complex between said protein and streptavidin or a streptavidin mutein via the peptide of the invention. Step (b) is contacting the biosensor with a second sample which can contain an analyte which analyte is capable of binding to said protein fused to the peptide of the invention, thereby allowing the formation of a complex between said protein fused to the peptide of the invention and the analyte, and in step (c) binding of the analyte to the protein is detected by use of a signal caused by the formation of the complex between said protein fused to the peptide of the invention and the analyte.

In a preferred embodiment of this detection method, the analyte is a protein, a protein domain or a peptide. This embodiment is thus in particular useful for studying protein-protein interactions and can thus be used in the field of proteomics. For example, the immobilized protein carrying the peptide of the invention can be an antibody fragment and the analyte can be a protein recognized by the antibody. As an exemplar model system the investigation of the lysozyme binding antibody D1.3 with (for example in form of its Fv-fragment having a ditag of the invention fused to the C-terminus of the VH domain) with lysozyme (see in this respect, Schmidt and Skerra, 1993, for example). A further example might be the interaction of human growth hormone (HGH) and human growth hormone receptor (Wells, A. J. 1996).

The analyte can also be a nucleic acid or an organic molecule. Examples of organic molecules the interaction of which can be investigated are metabolites, drugs or in general, any enzyme substrate, inhibitor or co-factor (cf. Busch et al (2000) describing the investigation of the inhibition of succinic semialdehyde dehyrogenase by AMP and ATP).

The biosensor can be any conventional biosensor which is used for bioanalytical purposes. Examples of such sensors are sensor used for surface plasmon resonance (e.g. "BIA-CORE®-chips"), silicon chips such as wafers or the E-SENSOR® of Motorola or glass substrates which are used in multi-array formats in proteomics and genomics.

In a further preferred embodiment of this detection method the signal caused by the formation of the complex between said protein and the analyte is a surface plasmon resonance signal. Accordingly, the biosensor is preferably a so-called BIACORE®-chip. The signal can, however, be also generated by a fluorescence or chromogenic label which is conjugated to one of the two complex partners. An advantage of the use of ditag or multitag of the present invention in an detection based on biosensors is that the biosensor can easily be regenerated. For this purpose, the protein immobilized on the surface of the chip via the ditag or multitag disclosed here is simply removed by washing the chip surface with a competitive streptavidin or streptavidin mutein ligand such as diaminobiotin and/or desthiobiotin. One such regenerated chip can thus be loaded with many different proteins of interest fused to the peptide of the invention. Therefore, the invention provides a convenient recyclable chip technology platform.

The invention further relates to an expression vector which contains a nucleic acid sequence, in particular a DNA sequence, coding for a peptide of the invention and which has one or more restriction cleavage sites 5' or/and 3' from this nucleic acid sequence, which allow introduction of another nucleic acid sequence, in particular a DNA sequence, coding for the protein to be expressed or for a protein part. The nucleic acid sequence is preferably under the control of a suitable promoter and, where appropriate, an operator. Preferably, at least one restriction cleavage site immediately adjoins the nucleic acid sequence coding for the peptide of the invention. However, it is also possible to provide the cleavage sites at some distance so that a spacer or linker region is provided between the peptide of the invention and the protein to be fused thereto. The linker region may also include or represent a cleavage site for a sequence-specific protease such as, for example, enterokinase or factor Xa so that the affinity tag can be cleaved off the desired protein after expression and, where appropriate, purification of the fusion protein.

With the aid of the expression vector of the invention it is made possible to arrange the nucleic acid sequence for a protein of interest with a nucleic acid sequence for the peptide of the invention in a simple manner and to obtain, after expression, a fusion protein of the invention. For example, inserting into a restriction cleavage site 5' from the nucleic acid sequence for the peptide of the invention the nucleic acid sequence for the protein to be fused thereto produces a fusion protein which has the streptavidin affinity-mediating ditag or multitag peptide of the invention at the carboxy terminus. Correspondingly, the affinity tag of the invention is located at the amino terminus if the nucleic acid sequence of the peptide to be fused is inserted into a restriction cleavage site in 3' direction.

The restriction cleavage site in the expression vector of the invention need not necessarily be located directly beside the first or last base of the nucleic acid sequence coding for the peptide. Preferably, however, it ought to be located such that the reading frame is not adversely affected during translation and a linkage of only a few, preferably not more than 10, additional amino acids is formed between the peptide and the amino acid sequence of the protein.

The invention further relates to a method for preparing a recombinant fusion protein, which involves introducing a nucleic acid sequence coding for the above-mentioned fusion protein into a suitable host cell. The preparation may also be carried out via in vitro expression, a nucleic acid sequence coding for the fusion protein being introduced into a cell extract or a cell lysate. The fusion protein of the invention can be obtained by expressing the nucleic acid sequence. The presence of the expression product can readily be detected via a conjugate of streptavidin or of a streptavidin mutant and a label or/and a solid phase. Furthermore, it is possible to isolate or purify the desired protein as fusion protein in a simple manner by using the streptavidin-binding properties of the ditag or multitag of the invention, streptavidin affinity chromatography being possible to be used, for example.

The nucleic acid sequence is preferably introduced into a suitable host cell or into cell lysate using an expression vector of the invention, which contains a nucleic acid coding for the desired fusion protein.

The conjugate of streptavidin and label preferably comprises a fluorescent label or/and an enzymatic label, in particular alkaline phosphatase or horseradish peroxidase. However, it is in principle possible to use any label which allows detection, for example also direct labels such as, for example, gold or latex particles or other labels known to the person skilled in the art.

An essential advantage of the peptides of the invention and the method of the invention for preparing recombinant fusion proteins is the possibility of purifying the expressed fusion protein readily by affinity chromatography via a column with immobilized streptavidin or an immobilized streptavidin mutant or in a batch process. While the ditags or multitags of the invention show high affinity for the receptor, they can nevertheless advantageously be eluted under very mild competitive conditions, for example by adding biotin or biotin-like compounds and in particular by adding 2-iminobiotin, lipoic acid, hydroxyphenylazobenzoic acid (HABA), dimethylhydroxyphenylazobenzoic acid (DM-HABA), diaminobiotin or/and desthiobiotin. Thus, the desired fusion protein can be liberated by competitive elution with streptavidin ligands in a simple manner and under mild conditions. Particular preference is given to the elution with biotin on the microscale (of microgram amounts) in batch format.

The streptavidin ligand that is used as competitor can also be an isolated peptide of the invention, a peptide containing only one streptavidin binding module of the peptide of the invention. This competitively binding ligand can also be fusion protein of the invention or a peptide or protein comprising one amino acid sequence Trp-X-His-Pro-Gln-Phe-Y-Z (SEQ ID NO:7) where X is any amino acid residue and Y and Z are in each case Gly or where Y is Glu and Z is Arg or Lys, i.e. a peptide or protein comprising, for example the Strep-Tag sequence.

Because of the very strong interaction between biotin and streptavidin, elution is particularly efficient when using biotin as competitor. When using biotin as competitor, however, a regeneration of the streptavidin receptor is impossible or only possible with difficulty. Therefore the use of biotin is preferred in particular if regeneration is not required, for example on a small scale (microgram amounts of streptavidin).

For carrying out the elution on a larger scale, including the industrial scale (mg to kg amounts of streptavidin), however, preference is given to using a competitor whose binding affinity for the streptavidin receptor is sufficiently high to effect effective elution but which can nevertheless be removed again from the streptavidin receptor in order to provide a regenerable system. On the large scale particular preference is therefore given to using desthiobiotin, iminobiotin, diaminobiotin, lipoic acid, HABA, or/and DM-HABA as competitor. On the large scale, lowering the pH is also an interesting alternative to competitive elution.

It is possible, for example, to use a streptavidin agarose matrix for streptavidin affinity chromatography. Preference is given to using Sepharose polysaccharide (Pharmacia) or Macro Prep (polymethacrylate; Bio Rad) or POROS (polystyrene (OH modified); PE Biosystems) as support material. Recently, also Superflow (crosslinked agarose, Sterogene) has been shown to be a valuable matrix to be used as carrier for streptavidin.

The invention further relates to a nucleic acid coding for a ditag peptide or multitag peptide of the invention. The invention also refers to a nucleic acid coding for a fusion protein comprising a ditag or multitag of the invention.

The invention furthermore comprises using streptavidin or/and a streptavidin mutein as receptor for binding a peptide of the invention.

The ditag or multitag of the invention makes rapid and safe detection of fusion proteins which are obtained, for example, as expression products possible. Furthermore, the fusion protein has exactly adjustable and advantageous properties of binding to streptavidin so that a simple purification of the expression product, which can also be carried out on the industrial scale, is made possible.

With the aid of the expression vector of the invention the expression of a fusion protein of the invention is made easier, and such an expression vector can be used universally for all proteins to be expressed. In the fusion protein the peptide of the invention does not interfere with the biological activity of the other part of the protein and therefore need not necessarily be cleaved off before further use. However, if for particular reasons removal of the peptide is desired, then the expression vector of the invention may also be constructed such that it has between the restriction cleavage site for introducing the nucleic acid sequence for the protein and the sequence coding for the peptide a further nucleic acid sequence coding for a specific protease cleavage site. Thus, after expression and, where appropriate, purification or detection of the expression product, cleavage of the peptide sequence can readily be carried out.

The following examples and the attached figures further illustrate the invention.

FIG. 1A shows the binding behavior of the fusion proteins when eluting with 2 ml of a non-competitive buffer. As FIG. 1A shows, the monotag fusion protein is already washed out of the column under non-competitive conditions, i.e. the band migrates downwards, while the two ditag fusion proteins remain stably immobilized in the upper part of the column.

FIG. 1B shows the binding behavior of the fusion proteins when eluting with 12 ml of a non-competitive buffer. Whereas here, too, the two ditag variants remain stably immobilized in the upper part of the column, the band of the monotag fusion protein has already broadened very much and has migrated through the gel.

FIG. 1C shows the binding behavior of the fusion proteins when eluting with 0.5 ml of a competitive buffer containing desthiobiotin.

FIG. 1D shows the binding behavior of the fusion proteins when eluting with 1.5 ml of a competitive buffer containing desthiobiotin.

Figure 1A:
FIGS. 1A-1D show the binding of cytochrome b562, red, with various affinity tags on STREP-TACTIN® Sepharose, where cytochrome b562-ditag 3 has been applied on the column denoted "L", cytochrome b562-ditag 2 has been applied on the column denoted "M" and cytochrome b562-monotag has been applied on the column denoted "R".
Figure 1B:
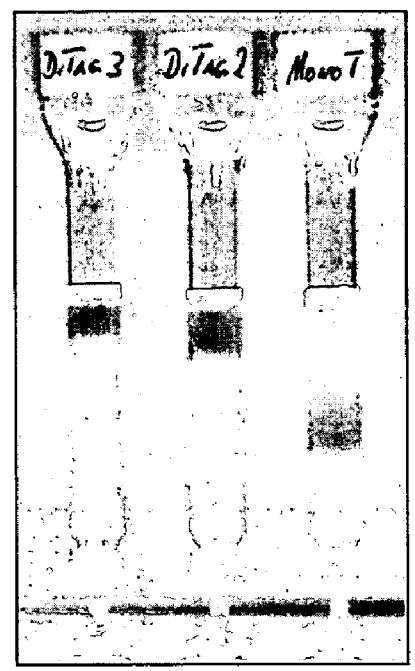
Figure 1C:
Figure 1D:
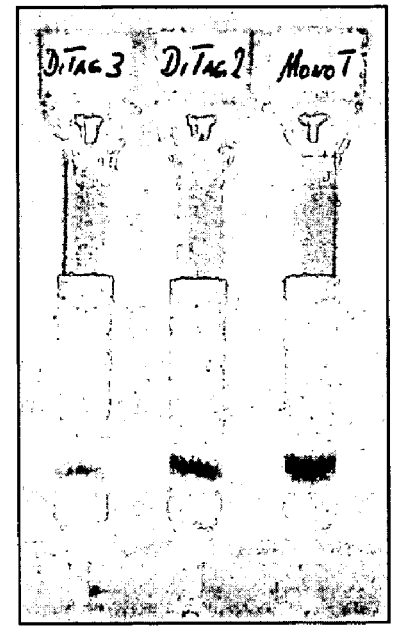

As can be seen from FIGS. 1C and 1D, the competitive displacement rate is nearly identical for all fusion proteins, meaning that under competitive conditions the two ditag fusion proteins are displaced from the column with the same efficiency as the monotag fusion protein.

Figure 2A:
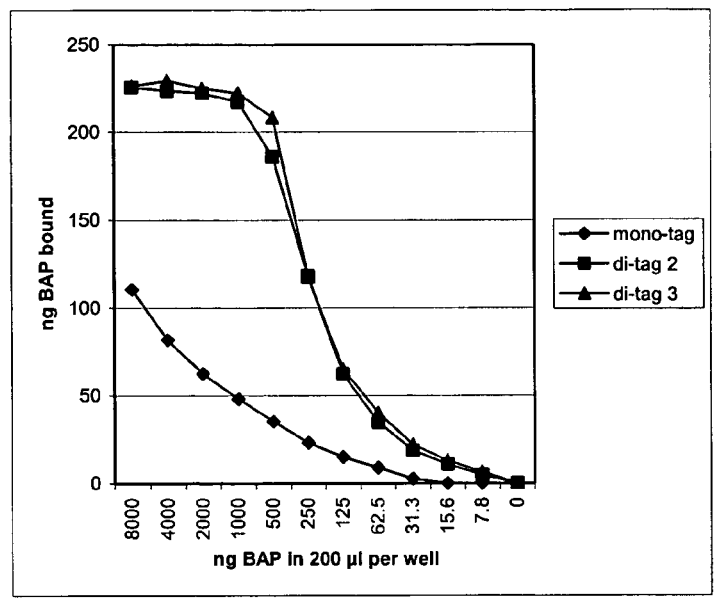

FIG. 2A shows the binding of bacterial alkaline phosphatase (BAP) to STREP-TACTIN® coated wells of a microtitre plate. For example, FIG. 2A shows the binding of BAP with C-terminal tag to STREP-TACTIN® coated wells of a microtitre plate. Different amounts of BAP fused to the various tags (mono-tag, di-tag 2, di-tag 3; see example 1 for sequences) were applied to microtiter plates with cavities that each have been previously coated with a constant amount of STREP-TACTIN®. After 3 washing cycles the bound BAP variant was measured by a colorimetric assay for BAP. The amount remaining after washing was plotted against the applied amount. FIG. 2A shows that the binding yield significantly improved for the di-tag variants versus the mono-tag.

Figure 2B:
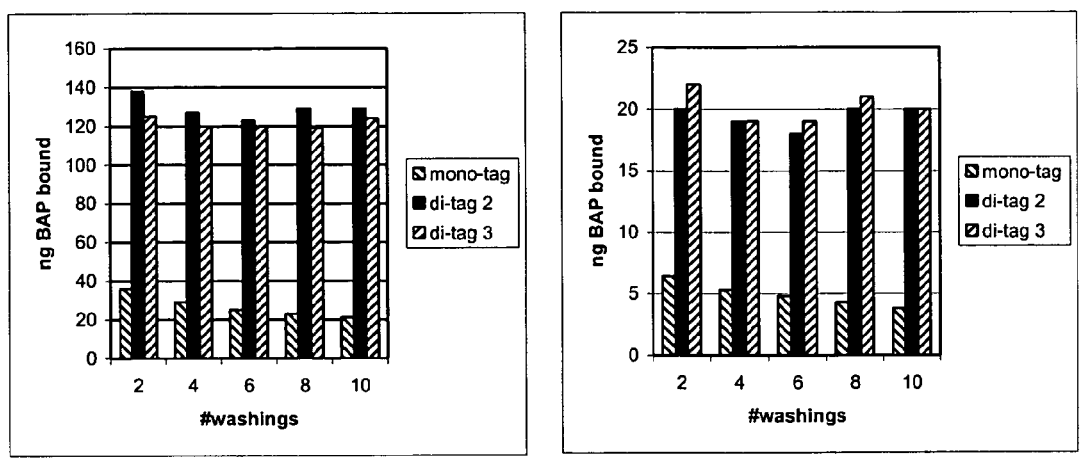

FIG. 2B shows the remaining BAP after an initial incubation of a given amount followed by various washing cycles. For example, the left panel of FIG. 2B illustrates the remaining BAP after an initial incubation of 500 ng in 200 µl followed by various washing cycles, and the right panel of FIG. 2B illustrates the remaining BAP after an initial incubation of 50 ng in 200 µl followed by various washing cycles. Identical amounts of BAP fused to the various tags (mono-tag, di-tag 2, di-tag 3; see example 1 for sequences) were applied to microtitre plates coated with constant amounts of STREP-TACTIN®. After various washing cycles the bound BAP variant was measured by a colorimetric assay for BAP. The amount remaining after washing was plotted against the number of washing cycles. It can be seen from FIG. 2B that the binding yield significantly improved for the di-tag variants versus the mono-tag.

Figures 1, 3A:
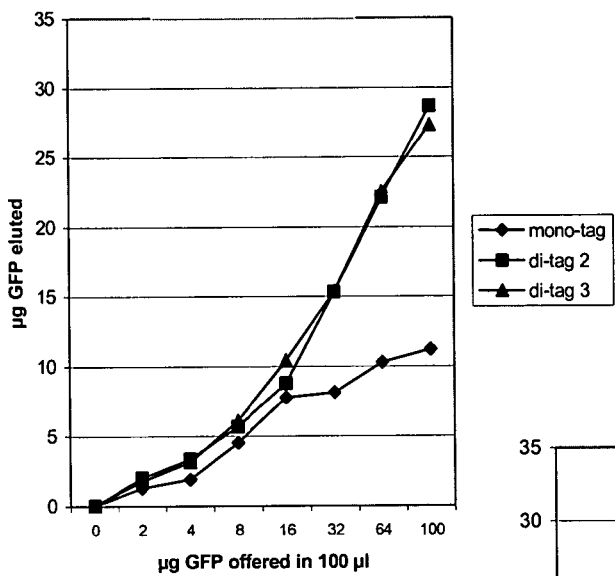
Figures 2, 3A:
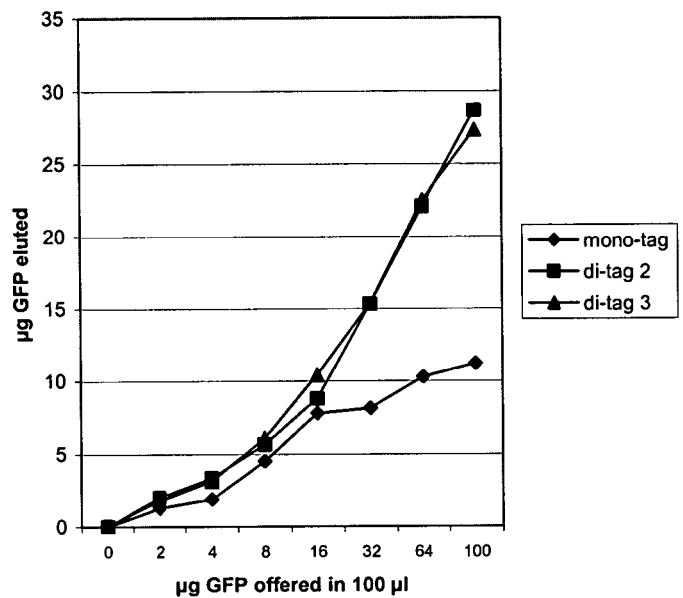

FIGS. 3A-1 and FIGS. 3A-2 show the purification of a Green Fluorescent Protein (GFP):tag fusion protein on STREP-TACTIN® coated magnetic beads.

FIGS. 3A-1 shows the yield of GFP-fused to the mono-tag, or di-tag 2, or di-tag 3 after purification with 2 mg magnetic beads coated with STREP-TACTIN®. The yield of GFP was determined and plotted against the initial amount GFP offered in a crude lysate. For example, FIGS. 3A-1 represents the purification of a GFP:tag fusion protein on 2 mg STREP-TACTIN® coated beads.

FIGS. 3A-2 shows the yield of GFP-fused to the mono-tag, or di-tag 2, or di-tag 3—after purification with 4 mg magnetic beads coated with STREP-TACTIN®. The yield of GFP was determined and plotted against the initial amount GFP offered in a crude lysate. For example, FIGS. 3A-2 represents the purification of a GFP:tag fusion protein on 4 mg STREP-TACTIN® coated beads.

Figure 3B:
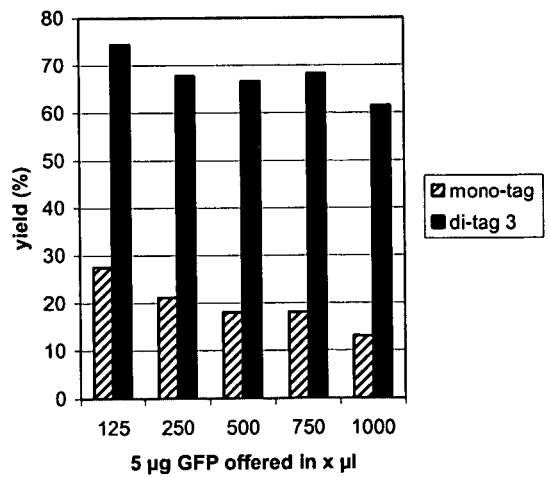

FIG. 3B shows the results of an experiment for testing whether the di-tag approach has also advantages for the batch purification of diluted recombinant proteins as it may be expected after poor expression. This experiment was performed as follows. 5 µg GFP were mixed with different volumes of a crude lysate and the recovery after purification was measured. Recovery was plotted against the initial volume lysate with which the 5 µg GFP were diluted. For example, FIG. 3B represents the purification of a GFP:tag fusion protein on 2 mg STREP-TACTIN® coated beads.

Figure 3C:
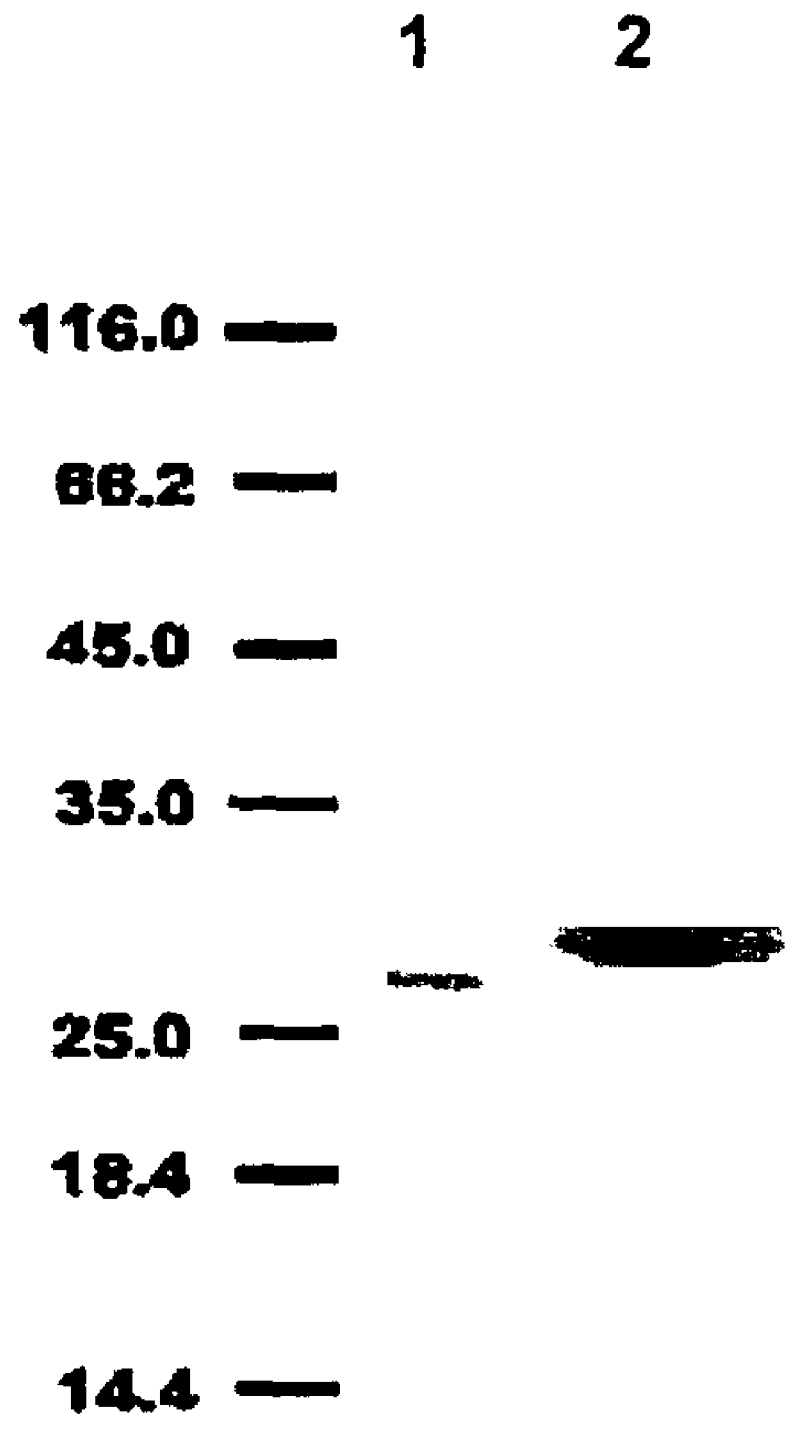

FIG. 3C shows an SDS page of purified GFP which is fused to ditag3 of the invention and to a Strep-mono-tag. On lane 1, 0.4 µg eluted GFP fused to the mono-tag and on lane 2, 1.5 µg eluted GFP fused to di-tag 3 were applied. As can be seen, highly pure recombinant can be produced, irrespective whether the Strep-mono-tag or di-tag is used. However, the di-tag may lead to clearly improved yields.

Figure 4A:
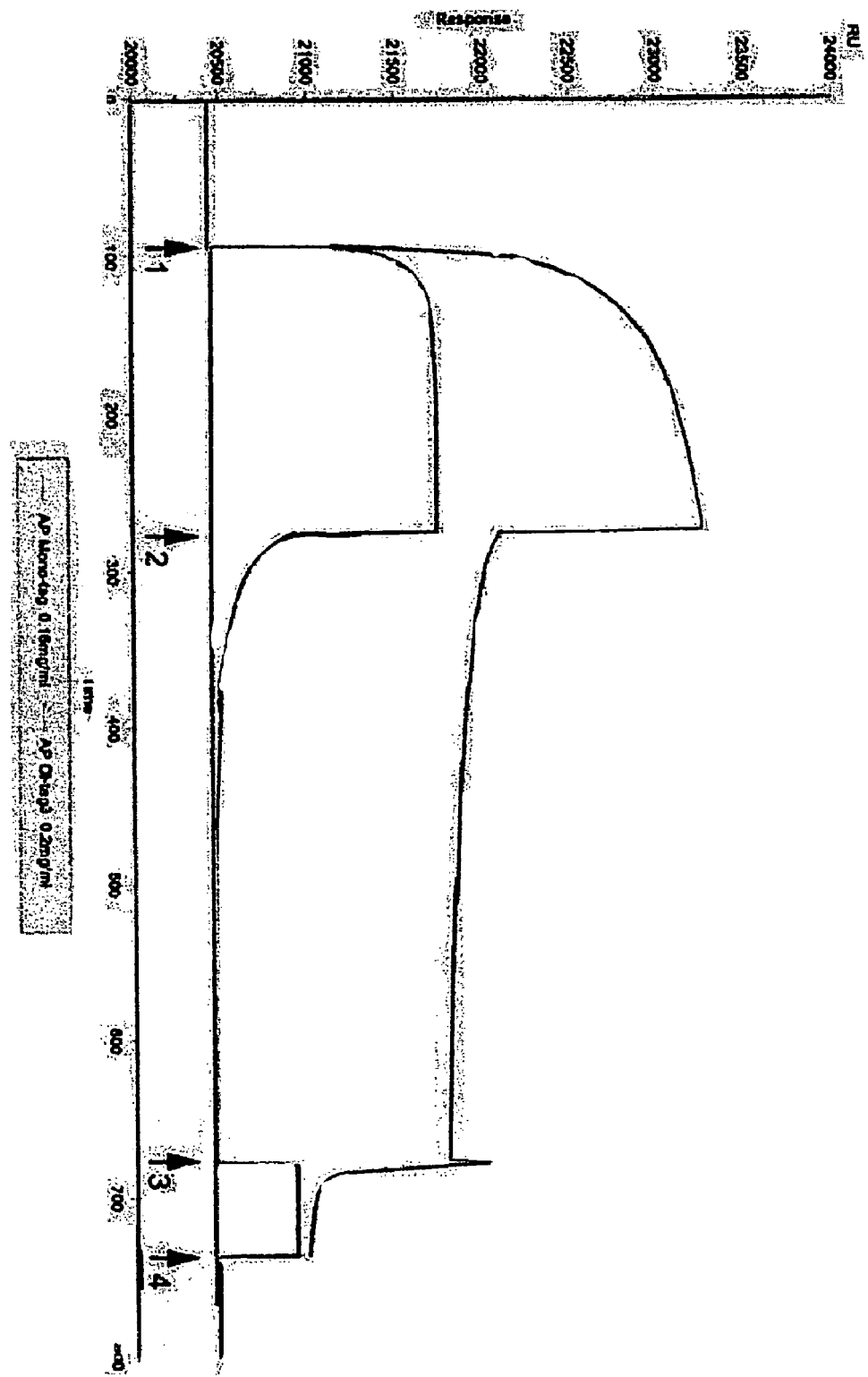
Figure 4B:
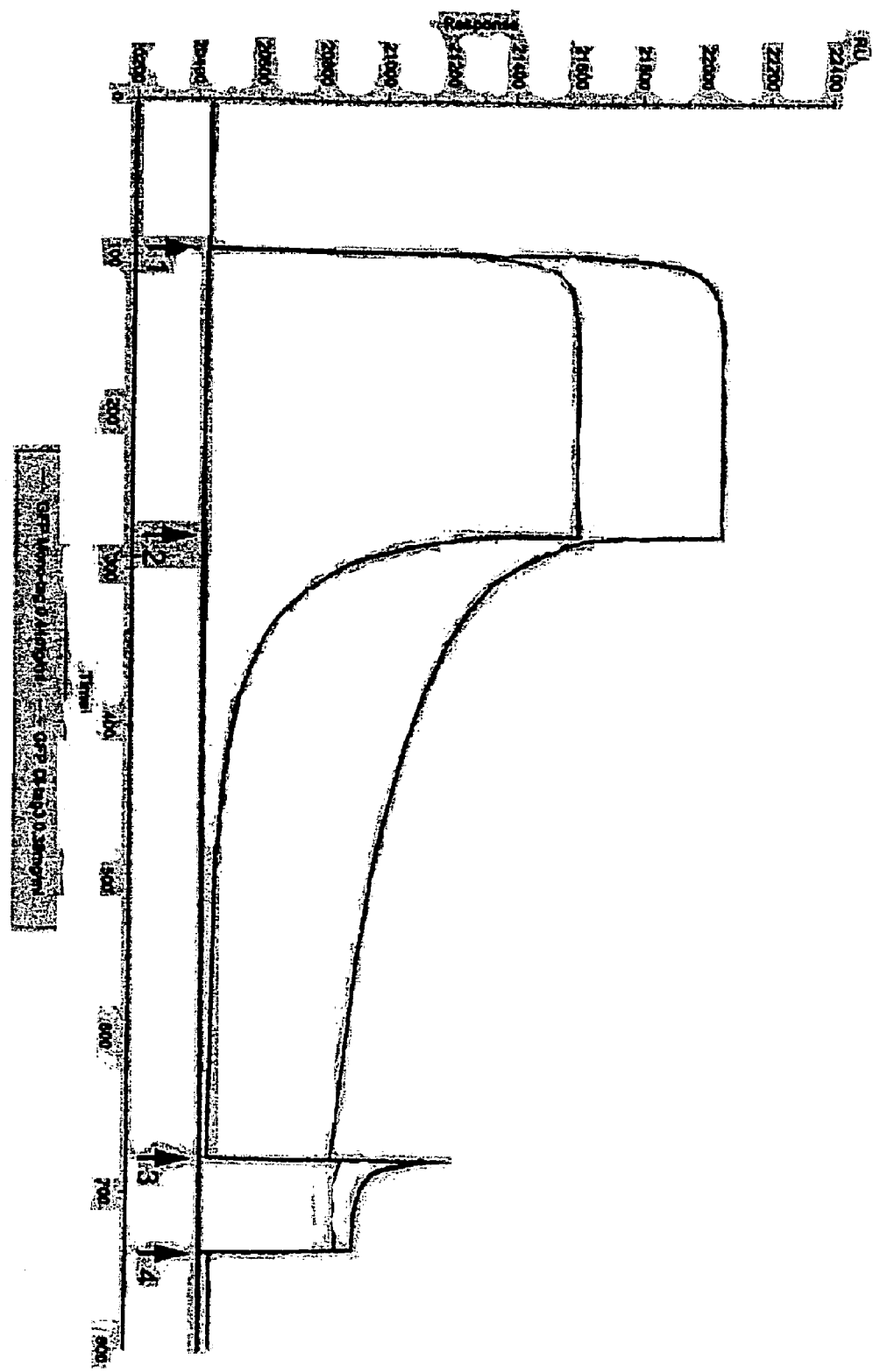

FIGS. 4A and 4B show BIACORE® sensorgrams of the binding/dissociation behaviour of the mono-strep-Tag: STREP-TACTIN® complex and the ditag 3:STREP-TACTIN® complex.

FIG. 4A shows a comparison of bacterial alkaline phosphatase (BAP) fused to the mono-tag with BAP fused to di-tag 3 (see example 1 for tag sequences). The sensorgram which had been obtained when BAP fused to the mono-tag had been applied at a concentration of 0.16 mg/ml is shown as the lower curve and that of BAP fused to di-tag 3 (0.2 mg/ml) is shown as the upper curve. The beginning of the association phase is marked with an arrow denoted "1. The change to the dissociation phase is marked with an arrow denoted "2. Start of desthiobiotin injection is marked with an arrow denoted "3" and termination of desthiobiotin injection is marked with an arrow denoted "4. Sensorgrams have not been corrected for RU changes induced by interaction between buffer component with the chip surface.

FIG. 4B shows the comparison of GFP fused to the mono-tag with GFP fused to di-tag3 (see example 1 for tag sequences). The sensorgram which had been obtained when GFP fused to the mono-tag had been applied at a concentration of 0.44 mg/ml is shown as the lower curve and that of BAP fused to di-tag 3 (0.39 mg/ml) is shown as the upper curve. The beginning of the association phase is marked with an arrow denoted "1". The change to the dissociation phase is marked with an arrow denoted "2". Start of desthiobiotin injection is marked with an arrow denoted "3" and termination of desthiobiotin injection is marked with an arrow denoted "4. Sensorgrams have not been corrected for RU changes induced by interaction between buffer component with the chip surface.

EXAMPLES

Example 1

Binding of Cytochrome b562 with Various Affinity Tags to STREP-TACTIN® Sepharose

*E. coli* cytochrome b562, red, with C-terminal STREP-TAG® is known to bind particularly poorly to immobilized streptavidin in comparison with other STREP-TAG® fusion proteins (Schmidt and Skerra, 1994).

In this experiment, binding of cytochrome b562, with various affinity tags at the C terminus (ditag 3; ditag 2; monotag), to 3 columns (L, M, R) with identical STREP-TACTIN® Sepharose material was compared:

---

L (ditag 3):
(SEQ ID NO: 14)
Cytochrome b562-WSHPQFEKGGGSGGGSGGGSWSHPQFEK-COOH

M (ditag 2):
(SEQ ID NO: 15)
Cytochrome b562-WSHPQFEKGGGSGGGSWSHPQFEK -COOH

R (monotag):
(SEQ ID NO: 2)
Cytochrome b562-WSHPQFEK-COOH (The underlined areas are the streptavidin-binding modules)

Defined purified amounts of the 3 different fusion proteins (700 µg with ditag 3; 800 µg with ditag 2; 950 µg with monotag) were loaded onto a STREP-TACTIN® Sepharose column with a bed volume of 2 ml and a biotin binding capacity of approx. 350 nmol per ml. After the protein solution had completely passed into the column, the latter was washed with buffer W (100 mM Tris-HCl pH 8.0; 150 mM NaCl) (non-competitive conditions). FIG. 1A and FIG. 1B show the location of the fusion protein after application of 2 ml and 12 ml of buffer W, respectively. It is clearly visible that the cytochrome b562-monotag fusion protein is already washed out of the column under non-competitive conditions and has already been removed completely from the upper part, while the two ditag variants remain comparatively stably immobilized in the upper part of the column. This finding leads to the immediate conclusion that it is possible to purify significantly larger amounts of cytochrome b562-ditag fusion protein on the same amount of identical column material. After washing with 12 ml of buffer W, the column was treated with buffer E (100 mM Tris-HCl pH 8.0; 150 mM NaCl; 2.5 mM desthiobiotin) (competitive conditions). FIGS. 1C and 1D show the location of the fusion protein after 0.5 and 1.5 ml of buffer E, respectively. The competitive displacement rate is nearly identical for all variants. This means that the two ditag fusion proteins in this chromatography experiment are displaced from the STREP-TACTIN® Sepharose column under competitive conditions with the same efficiency as the mono-tag fusion protein.

As can be seen from FIGS. 1C and 1D, the competitive displacement rate is nearly identical for all fusion proteins, meaning that under competitive conditions the two ditag fusion proteins are displaced from the column with the same efficiency as the monotag fusion protein.

Example 2

Immobilization of *E. coli* alkaline phosphatase (BAP) with C-terminal tags on STREP-TACTIN® coated wells of a microtiter plate:

Mono-tag vs Di-tag 2 and Di-tag 3 (cf. example 1 for tag sequences)

2.1 Amount Bound in Dependence of Amount Initially Applied

Various amounts of BAP fusion protein were diluted ad 200 µl with 25 mM Tris-HCl pH 7.8, 140 mM NaCl, 1 mM $MgCl_2$, 0.5 mM $ZnCl_2$, 0.25% w/v BSA and applied to microtiter plates (MTP) containing wells that were coated with STREP-TACTIN®. Then, the MTP's were incubated for 1 h at ambient temperature under shaking. After the binding step, each well was washed three times with 300 µl 25 mM Tris-HCl pH 7.5, 140 mM NaCl/0.1% v/v TWEEN-20 (TBS/Tween). Finally, bound BAP was detected by the addition of 2 mg/ml p-nitrophenylphosphate (p-NPP) and absorbance was monitored at 450 nm. The chromogenic reaction was performed in 200 µl 50 mM Tris-HCl pH 9.0, 140 mM NaCl, 5 mM $MgCl_2$. Quantification was performed by comparing the signals to a calibration curve that was achieved under the same conditions on the same plate in parallel, each calibration curve being determined for each BAP:tag fusion separately with known BAP amounts.

As shown in FIG. 2A, while half maximal binding (113 ng BAP) had already been reached for the di-tag fusions at an initial concentration of around 250 ng enzyme in 200 µl, an initial amount of 8000 ng enzyme was necessary for getting the same binding with the mono-tag fusion protein under the same conditions.

As shown in FIG. 2.1, while half maximal binding (113 ng BAP) had already been reached for the di-tag fusions at an initial concentration of around 250 ng enzyme in 200 µl, an initial amount of 8000 ng enzyme was necessary for getting the same binding with the mono-tag fusion protein under the same conditions.

2.2 Binding Stability in Dependence of the Number of Washing Cycles 50 or 500 ng BAP were diluted ad 200 µl with 25 mM Tris-HCl pH 7.8, 140 mM NaCl, 1 mM $MgCl_2$, 0.5 mM $ZnCl_2$, 0.25% w/v BSA and applied to microtiter plates (MTP) containing wells that were coated with STREP-TACTIN®. Then, MTP's were incubated for 1 h at ambient temperature under shaking. After the binding step, each well was washed various times with 300 µl 25 mM Tris-HCl pH 7.5, 140 mM NaCl/0.1% v/v TWEEN-20 (TBS/Tween). Finally, bound BAP was detected by performing a chromogenic reaction in each well by applying 200 µl 50 mM Tris-HCl pH 9.0, 140 mM NaCl, 5 mM $MgCl_2$, 2 mg/ml p-nitrophenylphosphate (p-NPP). Quantification of bound BAP was performed by comparing the signals to a calibration curve that was achieved under the same conditions on the same plate in parallel, each calibration curve being determined for each BAP:tag fusion separately with known BAP amounts.

While the immobilized amount of BAP remained essentially unchanged for the di-tag fusions, irrespective of the number of washing cycles, around 40% BAP fused to the mono-tag was washed off from washing cycle 2 to washing cycle 10 under the washing conditions applied (see FIG. 2B). Moreover, the absolute amount of enzyme that could be bound under these conditions was about 4 times higher for the di-tags in comparison to the mono-tag.

While the immobilized amount of BAP remained essentially unchanged for the di-tag fusions, irrespective of the number of washing cycles, around 40% BAP fused to the mono-tag was washed off from washing cycle 2 to washing cycle 10 under the washing conditions applied (see FIG. 2.2). Moreover, the absolute amount of enzyme that could be bound under these conditions was about 4 times higher for the di-tags in comparison to the mono-tag.

Example 3

Batch purification of wild-type green fluorescent protein (GFP) with C-terminal tags by STREP-TACTIN® coated magnetic beads:

Mono-tag vs Di-tag 2 and Di-tag 3 (cf. example 1 for tag sequences)

3.1 Determination of Yield with Different Amounts GFP Applied in a Constant Volume Using 2 and 4 mg Beads STREP-TACTIN® was covalently coupled to magnetic beads (1 µm diameter) at approximately 35 µg STREP-TACTIN® per mg beads. 100 mg of the resulting beads were washed 2 times in 4 ml TBS/Tween, 2 times in 100 mM phosphate pH 7.7, 0.5 M NaCl. Finally, 2 ml 50 mM Tris-HCl pH 7.7, 200 mM NaCl, 5 mM EDTA (=buffer W2) was added to the beads and a final volume of 2.4 ml resulted which was approximately equivalent to a 4% (w/v) suspension. 50 or 100 µl aliquots of that suspension (corresponding to 2 or 4 mg STREP-TACTIN® coated beads) were distributed on reaction vessels and the supernatant was discarded. Different amounts green fluorescent protein (GFP) were diluted ad 100 µl with a bacterial crude lysate prepared in buffer W2 and the spiked solution was mixed with 2 or 4 mg STREP-TACTIN® coated magnetic beads. The mixture was incubated at ambient temperature for 45 min. Then, the beads were washed 3 times with 250 µl buffer W2 and the purified GFP was one-step eluted by the addition of 10 mM biotin in 50 µl buffer W2.

The eluted GFP was quantified by a method according to Bradford and the amount was set into relation with the amount initially offered.

As shown in FIGS. 3A-1 and 3A-2, the yield of GFP di-tag fusions was doubled in comparison to the mono-tag fusion protein.

3.2 Determination of Yield Starting with a Constant Amount GFP (5 µg) Applied in Different Volumes Using 2 mg Beads The magnetic beads were pre-treated as described above (Example 3.1). 2 mg beads were distributed on the reaction vessels. 5 µg GFP with the different tags were diluted ad different volumes with a crude lysate at half concentration prepared in buffer W2. The spiked solution was mixed with 2 mg STREP-TACTIN® coated magnetic beads. The mixture was incubated at ambient temperature for 30 min. Then, the beads were washed 4 times with 250 µl buffer W2 for 3 min at each step and the purified GFP was one-step eluted by the addition of 10 mM biotin in 50 µl buffer W2. The eluted GFP was quantified by a method according to Bradford using purified GFP as standard and the amount was set into relation with the amount initially offered.

As can be seen from FIG. 3B the absolute yield is significantly higher for the di-tag 3 fusion protein at the initial concentrations tested here. Furthermore, the yield dropped in this experiment by approximately 50% from the highest to the lowest initial concentration for the mono-tag fusion protein while only 20% got lost for the di-tag 3 fusion protein. This shows that the initial concentration has a higher influence on the yield for the mono-tag fusion protein than for the di-tag 3 fusion protein.

3.3 Purification of GFP with Mono-Tag or di-Tag from a Standard *E. coli* Lysate After expression in *E. coli*, cells from 1 liter culture were pelleted and resuspended in 10 ml buffer W2 (see above). Cells were lysed via sonification and the lysate was centrifuged to remove insoluble materials. Then 60 µl of the supernatant were mixed with 40 µl buffer W2 and 2 mg magnetic beads coupled with STREP-TACTIN® were added. After an incubation of 30 minutes, the beads were washed 3 times with 250 µl of buffer W2. Finally, bound and purified GFP fusion protein was eluted with 50 µl of buffer W2 containing 10 mM biotin.

The yield of GFP fused to the mono-tag was 4.2 µg versus 17.6 µg GFP fused to di-tag 3.

In order to verify that purification via the di-tag leads not only to improved recovery of the recombinant protein via batch purification but also to highly pure material that can be compared in terms of purity with purifications via the mono-tag, the eluted protein fraction after application of biotin was analyzed via SDS-PAGE followed by Coomassie staining (FIG. 3C). On lane 1, 0.4 µg eluted GFP fused to the mono-tag and on lane 2, 1.5 µg eluted GFP fused to di-tag 3 were applied. As can be seen, highly pure recombinant can be produced, irrespective whether the Strep-mono-tag or di-tag is used. However, the di-tag may lead to clearly improved yields.

Example 4

Real-time STREP-TACTIN® binding behavior characterization of the di-tag3 versus the mono-tag when fused either to GFP or BAP and analyzed via plasmon surface resonance in a biacore apparatus on a CM5 chip.

The CM5 chip was activated with standard EDC/NHS chemistry and STREP-TACTIN® mutant 1 was coupled at 2722 RU (arbitrary units). Then purified BAP or GFP in buffer W was injected to the flow cell of the chip at a flow rate of 30 µl/min. After association phase was completed (180 seconds), running solution was changed to buffer W without protein and dissociation phase was observed for 400 seconds. Then, buffer W containing 2.5 mM desthiobiotin was injected for 60 seconds followed by change to buffer W again.

The following can be considered from the sensorgrams shown in FIGS. 4A and 4B:

1. The ditag3 mediates a higher enrichment of BAP or GFP at the STREP-TACTIN® coated chip surface.
2. While the mono-tag variant is nearly completely washed off the sensor chip as the sensorgram approaches the base-line during the dissociation phase, substantial amounts of the di-tag 3 variant remain on the chip during the same time
3. Desthiobiotin mediates fast removal of the remaining di-tag 3 variant (the increase/decrease of RU at the beginning/end of desthiobiotin application results from binding/removal of desthiotbiotin to/off STREP-TACTIN®)

Concluding, these experiments clearly demonstrate that the di-tag approach has great practical use for the immobilization of tagged proteins on solid surfaces and for the purification of small amounts in a batch format.

The following references are cited in this application

Argarana et al. (1986): Molecular cloning and nucleotide sequence of the streptavidin gene. Nucleic Acids Res. 14 1871-1882.

Bayer, E. A., et al. (1989): Postsecretory modifications of streptavidin. Biochem. J. 259, 369-376.

Busch, K., Piehler, J., Fromin, H. (2000), Plant Succinic Semialdehyde Dehydrogenase: Dissection of nucleotide binding by surface plasmon resonance and fluorescence spectroscopy. Biochemistry, 39, 10110-10117.

Devlin, J. J., Panganiban, L. C. & Devlin, P. E. (1990), Random peptide libraries: A source of specific protein binding molecules. Science 249, 404-406.

Lam, K. S., Salmon, E. S., Hersh, E. M., Hruby, V. J., Kazmierski, W. M. & Knapp, R. J. (1991). A new type of synthetic peptide library for identifying ligand-binding activity. Nature 354, 82-84.

Schmidt, T. G. M. & Skerra, A. (1993). The random peptide library-assisted engineering of a C-terminal affinity peptide, useful for the detection and purification of a functional Ig $F_v$ fragment. Prot. Engineering 6, 109-122.

Schmidt, T. G. M. & Skerra, A. (1994). One-step affinity purification of bacterially produced proteins by means of the 'Strep tag' and immobilized recombinant core streptavidin. J. Chromatogr. A676, 337-345.

Schmidt, T. G. M., Koepke, J., Frank, R. & Skerra, A. (1996). Molecular interaction between the Strep-tag affinity peptide and its cognate target streptavidin. J. Mol. Biol. 255, 753-766.

Skerra, A. & Schmidt, T. G. M. (1999). Applications of a Peptide Ligand for streptavidin: the Strep-tag. Biomolecular Engineering 16, 79-86.

Voss, S. & Skerra, A. (1997) Mutagenesis of a flexible loop in streptavidin leads to higher affinity for the Strep-tag II peptide and improved performance in recombinant protein purification. Protein Eng. 10, 975-982.

Weber, P. C., Pantoliano, M. W. & Thompson L. D. (1992). Crystal structure and ligand-binding studies of a screened peptide complexed with streptavidin. Biochemistry 31, 9350-9354.

Weber, P. C., M. W. Pantoliano and F. R. Salemme (1995). Crystallographic and thermodynamic comparison of structurally diverse molecules binding to streptavidin. Acta Cryst. D51: 590-596.

Wells, A. J. (1996). Binding in the growth hormone receptor complex. Proc. Natl. Acad. Sci. U.S.A. 93, 1-6.

Wilson, D. S., Keefe, A. D. and Szostak, D (2001). The use of mRNA display to select high-affinity protein-binding peptides. Proc. Natl. Acad. Sci. U.S.A., Vol. 98, No. 7, 3750-3755.
U.S. Pat. No. 5,506,121,
U.S. Pat. No. 6,103,493,
WO 86/02077,
DE 196 41876
U.S. Pat. No. 6,022,951,
WO 98/40396,
WO 96/24606.

The invention claimed is:

1. A fusion protein comprising a streptavidin-binding peptide linked to a protein sequence of interest, wherein the streptavidin-binding peptide comprises a sequential arrangement of two modules, wherein the streptavidin-binding peptide is located at the carboxy terminal end or at the amino terminal end of the protein sequence of interest, wherein each module binds at least one of a streptavidin or a streptavidin mutein, wherein the modules are different or identical and each of the modules comprises an amino acid sequence -His-Pro-Baa- in which Baa is selected from the group consisting of glutamine, asparagine and methionine, and wherein at least one of the modules comprises a sequence -His-Pro-Gln-Phe- (SEQ ID NO:6).

2. The fusion protein according to claim 1, wherein the protein sequence of interest is selected from the group consisting of a full-length protein, a protein mutant, and a protein fragment.

3. The fusion protein according to claim 1, wherein each module has a binding affinity of at least $Kd \leq 10$ mM.

4. The fusion protein according to claim 1, wherein at least one module binds competitively with biotin.

5. The fusion protein according to claim 1, wherein the streptavidin-binding peptide binds cooperatively to a single streptavidin tetramer or streptavidin dimer.

6. The fusion protein according to claim 1, wherein each module comprises a sequence -His-Pro-Gln-.

7. The fusion protein according to claim 1, wherein a distance between the at least two modules is between zero amino acids and 50 amino acids, inclusive.

8. The fusion protein according to claim 1, wherein at least one module comprises a sequence -Oaa-Xaa-His-Pro-Gln-Phe-Yaa-Zaa- (SEQ ID NO:7), where Oaa is Trp, Lys or Arg, Xaa is any amino acid, and wherein either Yaa and Zaa are both Gly, or wherein Yaa is Glu and Zaa is Lys or Arg.

9. The fusion protein according to claim 1, wherein at least one module comprises a sequence -Trp-Xaa-His-Pro-Gln-Phe-Yaa-Zaa- (SEQ ID NO:8), wherein Xaa is any amino acid, and wherein either Yaa and Zaa are both Gly, or Yaa is Glu and Zaa is Lys or Arg.

10. The fusion protein according to claim 1, wherein at least one module comprises a sequence -Trp-Ser-His-Pro-Gln-Phe-Glu-Lys- (SEQ ID NO:9).

11. The fusion protein according to claim 1, which comprises a sequence -Trp-Ser-His-Pro-Gln-Phe-Glu-Lys-(Xaa)n-Trp-Ser-His-Pro-Gln-Phe-Glu-Lys- (SEQ ID NO:3), wherein Xaa is any amino acid, and n is either 8 or 12.

12. The fusion protein according to claim 1, which comprises a sequence -Trp-Ser-His-Pro-Gln-Phe-Glu-Lys-(GlyGlyGlySer)n-Trp-Ser-His-Pro-Gln-Phe-Glu-Lys- (SEQ ID NO:11), and wherein n is either 2 or 3.

13. The fusion protein of claim 2 wherein said streptavidin binding peptide is located at the carboxy terminal of said protein sequence of interest.

14. The fusion protein of claim 2 wherein said streptavidin binding peptide is located at the amino terminal of said protein sequence of interest.

15. The fusion protein of claim 1, wherein said sequential arrangement of two modules forms part of a sequential arrangement of 3 modules.

16. The fusion protein of claim 1, wherein said sequential arrangement of two modules forms part of a sequential arrangement of 4 modules.

17. The fusion protein of claim 1, wherein said sequential arrangement of two modules forms part of a sequential arrangement of 5 modules.

* * * * *

SEQUENCE LISTING

```
<160> NUMBER OF SEQ ID NOS: 13

<210> SEQ ID NO 1
<211> LENGTH: 8
<212> TYPE: PRT
<213> ORGANISM: Artificial sequence
<220> FEATURE:
<223> OTHER INFORMATION: Peptide binding module

<400> SEQUENCE: 1

Trp Arg His Pro Gln Phe Gly Gly
1               5

<210> SEQ ID NO 2
<211> LENGTH: 8
<212> TYPE: PRT
<213> ORGANISM: Artificial sequence
<220> FEATURE:
<223> OTHER INFORMATION: Peptide binding module

<400> SEQUENCE: 2

Trp Ser His Pro Gln Phe Glu Lys
1               5

<210> SEQ ID NO 3
<211> LENGTH: 24
<212> TYPE: PRT
<213> ORGANISM: Artificial sequence
<220> FEATURE:
<223> OTHER INFORMATION: Peptide binding module
<220> FEATURE:
<221> NAME/KEY: MOD_RES
<222> LOCATION: (9)..(16)
<223> OTHER INFORMATION: Xaa=any amino acid

<400> SEQUENCE: 3

Trp Ser His Pro Gln Phe Glu Lys Xaa Xaa Xaa Xaa Xaa Xaa Xaa Xaa
1               5                   10                  15

Trp Ser His Pro Gln Phe Glu Lys
            20

<210> SEQ ID NO 4
<211> LENGTH: 24
<212> TYPE: PRT
<213> ORGANISM: Artificial sequence
<220> FEATURE:
<223> OTHER INFORMATION: Peptide binding module
<220> FEATURE:
<221> NAME/KEY: MOD_RES
<222> LOCATION: (9)..(18)
<223> OTHER INFORMATION: Xaa=any amino acid
<220> FEATURE:
<221> NAME/KEY: MOD_RES
<222> LOCATION: (22)..(24)
<223> OTHER INFORMATION: Xaa=any amino acid

<400> SEQUENCE: 4

Trp Ser His Pro Gln Phe Glu Lys Xaa Xaa Xaa Xaa Xaa Xaa Xaa Xaa
1               5                   10                  15

Xaa Xaa His Pro Gln Xaa Xaa Xaa
```

-continued

```
<210> SEQ ID NO 5
<211> LENGTH: 19
<212> TYPE: PRT
<213> ORGANISM: Artificial sequence
<220> FEATURE:
<223> OTHER INFORMATION: Peptide binding module
<220> FEATURE:
<221> NAME/KEY: MOD_RES
<222> LOCATION: (4)..(16)
<223> OTHER INFORMATION: Xaa=any amino acid

<400> SEQUENCE: 5

His Pro Gln Xaa Xaa Xaa Xaa Xaa Xaa Xaa Xaa Xaa Xaa Xaa Xaa Xaa
1               5                   10                  15

His Pro Gln

<210> SEQ ID NO 6
<211> LENGTH: 4
<212> TYPE: PRT
<213> ORGANISM: Artificial sequence
<220> FEATURE:
<223> OTHER INFORMATION: Peptide binding module

<400> SEQUENCE: 6

His Pro Gln Phe
1

<210> SEQ ID NO 7
<211> LENGTH: 8
<212> TYPE: PRT
<213> ORGANISM: Artificial sequence
<220> FEATURE:
<223> OTHER INFORMATION: Peptide binding module
<220> FEATURE:
<221> NAME/KEY: MOD_RES
<222> LOCATION: (1)..(1)
<223> OTHER INFORMATION: Xaa=Trp, Lys, or Arg
<220> FEATURE:
<221> NAME/KEY: MOD_RES
<222> LOCATION: (2)..(2)
<223> OTHER INFORMATION: Xaa=any amino acid
<220> FEATURE:
<221> NAME/KEY: MOD_RES
<222> LOCATION: (7)..(8)
<223> OTHER INFORMATION: Xaa(7,8)=Gly or Xaa(7)=Glu and Xaa(8)=Lys or
      Arg

<400> SEQUENCE: 7

Xaa Xaa His Pro Gln Phe Xaa Xaa
1               5

<210> SEQ ID NO 8
<211> LENGTH: 8
<212> TYPE: PRT
<213> ORGANISM: Artificial
<220> FEATURE:
<223> OTHER INFORMATION: Peptide binding module
<220> FEATURE:
<221> NAME/KEY: MOD_RES
<222> LOCATION: (2)..(2)
<223> OTHER INFORMATION: Xaa=any amino acid
<220> FEATURE:
<221> NAME/KEY: MOD_RES
<222> LOCATION: (7)..(8)
<223> OTHER INFORMATION: Xaa(7,8)=Gly or Xaa(7)=Glu and Xaa(8)=Lys or
      Arg
```

<400> SEQUENCE: 8

Trp Xaa His Pro Gln Phe Xaa Xaa
1               5

<210> SEQ ID NO 9
<211> LENGTH: 8
<212> TYPE: PRT
<213> ORGANISM: Artificial sequence
<220> FEATURE:
<223> OTHER INFORMATION: Peptide binding module

<400> SEQUENCE: 9

Trp Ser His Pro Gln Phe Glu Lys
1               5

<210> SEQ ID NO 10
<211> LENGTH: 36
<212> TYPE: PRT
<213> ORGANISM: Artificial sequence
<220> FEATURE:
<223> OTHER INFORMATION: Peptide binding module
<220> FEATURE:
<221> NAME/KEY: MOD_RES
<222> LOCATION: (9)..(28)
<223> OTHER INFORMATION: Xaa=any amino acid, and up to 15 Xaa residues
      may be missing from the sequence shown.

<400> SEQUENCE: 10

Trp Ser His Pro Gln Phe Glu Lys Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Trp Ser His Pro
            20                  25                  30

Gln Phe Glu Lys
        35

<210> SEQ ID NO 11
<211> LENGTH: 36
<212> TYPE: PRT
<213> ORGANISM: Artificial sequence
<220> FEATURE:
<223> OTHER INFORMATION: Peptide binding module
<220> FEATURE:
<221> NAME/KEY: REPEAT
<222> LOCATION: (9)..(28)
<223> OTHER INFORMATION: Repeat length of GlyGlyGlySer motif is
      variable; up to 4 GlyGlyGlySer repeats may be missing in this
      region as compared to the sequence shown.

<400> SEQUENCE: 11

Trp Ser His Pro Gln Phe Glu Lys Gly Gly Gly Ser Gly Gly Gly Ser
1               5                   10                  15

Gly Gly Gly Ser Gly Gly Gly Ser Gly Gly Gly Ser Trp Ser His Pro
            20                  25                  30

Gln Phe Glu Lys
        35

<210> SEQ ID NO 12
<211> LENGTH: 4
<212> TYPE: PRT
<213> ORGANISM: Artificial sequence
<220> FEATURE:
<223> OTHER INFORMATION: Peptide binding module

<400> SEQUENCE: 12

Ile Gly Ala Arg
1

```
<210> SEQ ID NO 13
<211> LENGTH: 4
<212> TYPE: PRT
<213> ORGANISM: Artificial sequence
<220> FEATURE:
<223> OTHER INFORMATION: Peptide binding module

<400> SEQUENCE: 13

Val Thr Ala Arg
1
```